US006887474B1

(12) United States Patent
Stewart et al.

(10) Patent No.: US 6,887,474 B1
(45) Date of Patent: May 3, 2005

(54) COMPOSITIONS AND METHODS FOR PRODUCING VASCULAR OCCLUSION

(75) Inventors: Michael William Stewart, St Albert (CA); Roland Henryk Person, Edmonton (CA); Antoine Noujaim, Edmonton (CA)

(73) Assignee: ViRexx Medical Corporation, Alberta (CA)

( * ) Notice: Subject to any disclaimer, the term of this patent is extended or adjusted under 35 U.S.C. 154(b) by 0 days.

(21) Appl. No.: 09/438,944

(22) Filed: Nov. 12, 1999

Related U.S. Application Data

(63) Continuation of application No. PCT/IB99/01899, filed on Nov. 10, 1999.
(60) Provisional application No. 60/108,129, filed on Nov. 12, 1998.

(51) Int. Cl.[7] .................... A61K 39/395; A61K 39/385; C07K 14/435; C07K 16/28; C07K 14/705
(52) U.S. Cl. ................ 424/178.1; 424/134.1; 424/135.1; 424/136.1; 424/138.1; 424/155.1; 424/195.11; 530/380; 530/387.3; 530/387.7; 530/388.7; 530/388.8; 530/391.7; 530/399
(58) Field of Search ............................. 435/69.7, 174, 435/775; 424/134.1, 135.1, 136.1, 138.1, 155.1, 178.1, 195.11; 530/380, 387.3, 387.7, 388.7, 388.8, 391.7; 536/23.1

(56) References Cited

U.S. PATENT DOCUMENTS 6,093,399 A * 7/2000 Thorpe et al.
6,218,513 B1 * 4/2001 Anthony-Cahill et al.

FOREIGN PATENT DOCUMENTS

WO PCT/US95/07439 1/1996
WO PCT/US98/01012 7/1998

OTHER PUBLICATIONS

Bensimon et al Science 265:2096–2099 1994.*
Xianming Huang et al. Science 275:547–550, Jan. 1997.*
Thorpe P.: "Antibody directed targeting of tumor vasculature (Meeting abstract)", Proc Annu Meet Am Assoc Cancer Res, vol. 37, p 668, 1996.
Barinaga M.: "Designing therapies that target tumor blood vessels", Science, vol. 275, pp 482–484, Jan. 1997.
Ohuchida, Shuichi et al.: "Synthesis of Thromboxane A Analogues: DL–9, 11:11, 12–Dideoxa–9, 11:11, 12–diepi-thiothromboxane A", Journal of American Chemical Society, vol. 103, pp. 4597–4599, (1981).
Stewart, Michael W. et al.: "Platelet activation by a novel solid–phase agonist: effects of VWF immobilized on polystyrene beads", British Journal of Haematology, vol. 97, pp. 321–329 (1997).
Kulkarni, Suhasini et al.: "A revised model of platelet aggregation", The Journal of Clinical Investigation, vol. 105 (6), pp. 783–791 (2000).
Ruggeri, Zaverio M.: "Old concepts and new developments in the study of platelet aggregation", The Journal of Clinical Investigation, vol. 105 (6), pp. 699–701 (2000).
Falati, Shahrokh et al.: "Glycoprotein Ib–V–IX, a Receptor for von Willebrand Factor, Couples Physically and Functionally to the Fc Receptor y–Chain, Fyn and Lyn to Activate Human Platelets", Blood, vol. 94 (5), pp. 1648–1656 (1999).
Kaufman, Randal J. et al.: "Regulation of Factor VIII Expression and Activity by von Willebrand Factor", Thrombosis and Haemostasis, vol. 82 (2), pp. 201–208 (1999).
Ruggeri, Zaverio M.: "Structure and Function of von Willebrand Factor", Thrombosis and Haemstasis, vol. 82 (2), pp. 576–584 (1999).
Mann, Kenneth G.: "Biochemistry and Pphysiology of Blood Coagulation", Thrombosis and Haemostasis, vol. 82 (2), pp. 165–174 (1999).

* cited by examiner

Primary Examiner—Christina Chan
Assistant Examiner—F. Pierre VanderVegt
(74) Attorney, Agent, or Firm—William J. Bundren, Esq

(57) ABSTRACT

The present invention relates generally to methods and compositions for targeting, delivering, and activating platelet-dependent vascular occlusion agents. In particular, antibodies carrying platelet binding agents are targeted to hyperplastic cells or tissues, such as the vasculature of solid tumor masses; the platelet binding agent then binds and activates platelets, which in turn bind and activate other platelets. This process results in the formation of a platelet-mediated thrombus-causing vessel occlusion.

5 Claims, No Drawings

SEQUENCE LISTING

<160> NUMBER OF SEQ ID NOS: 6

<210> SEQ ID NO 1
<211> LENGTH: 12
<212> TYPE: PRT
<213> ORGANISM: human MUC-1

<400> SEQUENCE: 1

Gly Val Thr Ser Ala Pro Asp Thr Arg Pro Ala Pro

-continued

```
1               5               10
```

<210> SEQ ID NO 2
<211> LENGTH: 5
<212> TYPE: PRT
<213> ORGANISM: human MUC-1

<400> SEQUENCE: 2

```
Pro Asp Thr Arg Pro
1               5
```

<210> SEQ ID NO 3
<211> LENGTH: 7
<212> TYPE: PRT
<213> ORGANISM: human MUC-1

<400> SEQUENCE: 3

```
Thr Ser Ala Pro Asp Thr Arg
1               5
```

<210> SEQ ID NO 4
<211> LENGTH: 5
<212> TYPE: PRT
<213> ORGANISM: human MUC-1

<400> SEQUENCE: 4

```
Ala Pro Asp Thr Arg
1               5
```

<210> SEQ ID NO 5
<211> LENGTH: 7
<212> TYPE: PRT
<213> ORGANISM: human MUC-1

<400> SEQUENCE: 5

```
Thr Ser Ala Pro Asp Thr Arg
1               5
```

<210> SEQ ID NO 6
<211> LENGTH: 8
<212> TYPE: PRT
<213> ORGANISM: human MUC-1

<400> SEQUENCE: 6

```
Ser Ala Pro Asp Thr Arg Pro Ala
1               5
```

COMPOSITIONS AND METHODS FOR PRODUCING VASCULAR OCCLUSION

This application is a continuation of application Ser. No. PCT/IB99/01899, filed Nov. 10, 1999, which claims the benefit of the filing date of provisional application Ser. No. 60/108,129, filed Nov. 12, 1998.

CROSS REFERENCE TO RELATED APPLICATIONS

Not Applicable

FEDERAL SPONSORSHIP

Not Applicable

BACKGROUND OF THE INVENTION

1. Field of the Invention

The present invention is directed to compositions and methods for producing a therapeutic benefit by producing vascular occlusion using platelet activation as the initiating event. Compositions and methods of the invention involve targeting platelets to a site, such as a tumor site, using a binding agent, such as a bi-functional molecule, a portion of which binds to the site and another portion of which binds or immobilizes a platelet binding agent, such as circulating von Willebrand Factor (VWF).

2. Description of the Related Art

Platelets function in the body to limit blood loss in the event of vascular damage. Normally, platelets circulate throughout the body with other cellular components of blood, bathed in a mixture of various plasma proteins, many of which play key roles in the clotting process. Upon exposure of vascular sub-endothelium, a complex series of events occurs to limit the loss of blood from the damaged vessel. Platelets contacting components of the exposed sub-endothelium: 1) bind and adhere, 2) spread across the exposed surface, 3) activate as evidenced by release of granule contents, 4) aggregate and recruit other platelets from the blood stream, and 5) form an efficient plug stemming the flow of blood from the vessel.

In contrast to the coagulation cascade, i.e., the sequential conversion of coagulation protein zymogens into active enzymes and which ultimately ends in the conversion of fibrinogen to fibrin, platelets bind specifically to the damaged area and are held together by bridging molecules that bind to specific receptors on the platelet surface. The initial bridging between platelets and the sub-endothelium is dependent on the interaction between the glycoprotein Ib (GPIb) receptor on the surface of the platelet and VWF in the subendothelium (i.e., immobilized VWF). This interaction in itself is unique since normal platelets circulating in the blood contacting soluble VWF are not activated, nor do they bind to the soluble VWF. In vitro experimentation has confirmed that immobilization of the soluble VWF to a surface facilitates binding and activation of platelets (Stewart et al, *British Journal of Haematology*, 97:231–9, 1997). Upon activation of the platelet an additional receptor, glycoprotein IIb/IIIa (GPIIb/IIIa), is altered and enables the binding of several plasma proteins, thereby promoting platelet/platelet binding (Savage et al, *Journal of Biological Chemistry*, 267:11300–6, 1992). In addition to fibrinogen, soluble VWF binds to the activated GPIIb/IIIa receptor, in turn becoming immobilized and capable of binding other platelets via GPIb and GPIIb/IIIa.

Hyperactive platelets induce thrombus formation at inopportune times resulting in reduced blood supply to key organs and tissues. A prime example is thrombus formation induced by blood flowing through a stenotic (narrowed) vessel supplying the heart. Reduction of the flow of blood to the heart muscle leads to infarction and eventually heart attack (cardiac cell death). Cerebral ischemia (transient ischemic attack, TIA; stroke) occurs when an embolus or thrombus occludes blood vessels feeding the brain.

Other pathological states exist which are caused by platelet activation due to an antibody-mediated process. Heparin-induced thrombocytopenia (HIT) is characterized by a dramatic loss in platelet numbers and thrombus formation at sites of pre-existing pathology. Patients receiving heparin, as an anticoagulant to promote blood flow, occasionally (1 to 5% of all patients receiving un-fractionated heparin) produce an antibody that binds to heparin in complex with a platelet granule protein (Kelton et al, *Blood*, 83:3232–9, 1994). The binding of the antibody to the heparin/protein complex on the surface of the platelet induces rapid platelet activation and localized thrombus formation. This in turn leads to infarction of the affected area.

Thrombosis is a well-described consequence of cancer. Controversy exists as to whether the presence of a hypercoagulable state is predictive of cancer. Many studies have been conducted demonstrating a prothrombotic tendency with most neoplasias. It has been suggested that thrombosis is the most frequent complication in patients with overt malignant disease.

Concern has arisen regarding the potential risk of enhancing thromboembolic disease as a result of current therapy regimens (surgical or chemotherapeutic). In some instances, oral anticoagulation is initiated to prevent possible thrombotic complications. A key to the development of successful anti-tumor agents is the ability to design agents that will selectively kill tumor cells, while exerting relatively little, if any, untoward effects against normal tissues. This goal has been elusive to achieve in that there are few qualitative differences between neoplastic and normal tissues. Because of this much research over the years has focused on identifying tumor-specific "marker antigens" that can serve as immunological targets both for chemotherapy and diagnosis. Many tumor-specific or quasi-tumor-specific (tumor-associated) markers have been identified as tumor cell antigens that can be recognized by specific antibodies.

Unfortunately, it is generally the case that tumor specific antibodies will not in and of themselves exert sufficient anti-tumor effects to make them useful in cancer therapy. In contrast with their efficacy in lymphomas, immunotoxins have proven to be relatively ineffective in the treatment of solid tumors such as carcinomas. The principal reason for this is that solid tumors are generally impermeable to antibody-sized molecules: specific uptake values of less than 0.001% of the injected dose/g of tumor are not uncommon in human studies. Furthermore, antibodies that enter the tumor mass do not distribute evenly for several reasons. First, the dense packing of tumor cells and fibrous tumor stromas present a formidable physical barrier to macromolecular transport and combined with the absence of lymphatic drainage create an elevated interstitial pressure in the tumor core which reduces extravasation and fluid convection. Second, the distribution of blood vessels in most tumors is disorganized and heterogeneous; as a result, some tumor cells are separated from extravasating antibody by large diffusion distances. Third, all of the antibody entering the tumor may become absorbed in perivascular regions by the first tumor cells encountered, leaving none to reach tumor cells at more distant sites.

One approach would be to target cytotoxic agents or thrombus-inducing agents to the vasculature of the tumor rather than to the tumor.

The present inventors propose that this approach offers several advantages over direct targeting of tumor cells. First, the target cells are directly accessible to intravenously administered therapeutic agents permitting rapid localization of a high percentage of the injected dose. Second, since each capillary provides oxygen and nutrients for thousands of cells in its surrounding 'cord' of tumor, even limited damage to the tumor vasculature could produce an avalanche of tumor cell death. Finally, the outgrowth of mutant endothelial cells lacking the target antigen is unlikely because they are normal cells.

SUMMARY OF THE INVENTION

The present invention relates to therapeutic methods and compositions for targeting tissues and/or organs, and associated vasculature, which are hyperplastic or neoplastic in nature, using agents that induce thrombus formation via localized platelet activation. The composition uses an agent for capturing platelets at a predetermined site and an agent for activating the captured platelets. In some embodiments of the invention, a single agent both captures and activates the platelets. The method utilizes localized platelet collection and activation, which produces subsequent thrombus formation, thereby limiting the blood supply to the target area, without inducing a generalized or systemic prothrombotic state.

The invention also may employ bifunctional agents having a targeting component capable of binding tumor-associated antigens and/or antigens expressed on tumor vasculature, and a platelet-specific recognition component capable of binding and capturing platelets.

Purposeful induction of thrombosis in a cancer patient appears, at first glance, to be counter-intuitive, since inducing thrombosis in a cancer patient is well known to contribute significantly to patient morbidity and mortality.

The present invention, targeted platelet-mediated occlusion, is based on the site specific induction of thrombosis, utilizing the body's natural capacity to produce a thrombus in response to immobilized von Willebrand factor (VWF) or other locally acting platelet activation agents. Although VWF circulates in the blood stream in soluble form, it is not until the molecule is exposed as part of the subendothelium or binds to exposed collagen from the subendothelium that it is capable of capturing platelets and inducing platelet activation.

Using a bifunctional targeting agent directed toward a predetermined site or molecule (e.g. a tumor-specific or tumor-associated antigen, ligand/receptor complex), VWF is immobilized at the site, thereby inducing localized platelet capture and activation leading to thrombosis and cessation of blood flow to the local area. Cells, including tumor cells, diminish or die as a result of loss of localized blood flow. This approach avoids systemic platelet activation and thrombosis relying on the fact that immobilized VWF (not soluble VWF) will capture and activate a circulating platelet. Thus, the methods and compositions of the present invention are an indirect means of treating a pathological condition, such as cancer or hyperplastic cells.

In a manner similar to an existing pathological condition (i.e. Heparin-Induced Thrombocytopenia, HIT), localized platelet activation can be enhanced via an Fc-mediated process by incorporating a human Fc fragment into the bifunctional anti-tumor-associated or tumor-specific antigen or ligand/receptor complex targeting agent.

Platelet activation in HIT syndrome results in localized thrombosis and cessation of blood flow to the affected area. This leads to death of the local tissue.

The extent and degree of site-specific thrombosis can be controlled in a variety of ways. Inhibition of platelet activation through the use of anti-platelet agents (e.g. GPIIb/IIIa inhibitors, aspirin, dipyridamole, etc.) decreases the propensity to induce a thrombus, in a defined, titratable manner. Altering local blood flow, blood pressure and tissue temperature can also serve as means of controlling local platelet activation to a stimulus.

Typical vascularized tumors are the solid tumors, particularly carcinom as, which require a vascular component for the provision of oxygen and nutrients. Exemplary solid tumors to which the present invention is directed, include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like.

A preferred method of the invention includes preparing a binding agent, such as an antibody or antibody-like molecule, that recognizes an antigen or other ligand associated with the vascular endothelial cells of the vascularized tumor mass; linking or operatively attaching the antibody to the selected agents to form an antibody-agent conjugate and introducing the antibody-agent conjugate into the bloodstream of an animal, such as a human patient or a test animal. As used herein however, the term "antibody" is intended to refer broadly to any immunologic binding agent such as IgG, IgM, IgA, IgE, F(ab')$_2$, a univalent fragment such as Fab', Fab, Dab, as well as engineered antibodies such as single chain antibodies, covalently-linked single chain antibodies, recombinant antibodies, humanized antibodies, bispecific antibodies, and the like.

As noted above, a solution to the problem of poor penetration of antibodies into solid tumors is to attack the endothelial cells (EC) lining the blood vessels in the tumor. This approach offers several advantages over direct targeting of tumor cells. First, the target cells are directly accessible to intravenously administered therapeutic agents permitting rapid localization of high percentage of the injected dose. Second, since each capillary provides oxygen and nutrients for thousands of cells in its surrounding 'cord' of tumor even limited damage to the tumor vasculature could produce extensive tumor cell death. Finally, endothelial cells are similar in different tumors, making it feasible to develop a single reagent for treating numerous types of cancer.

An example of one such reagent would be that which recognizes a complex of VEGF and its receptor. Such an agent would be fashioned to uniquely recognize the combination of VEGF and the VEGF receptor, having little or no effect on either the ligand (VEGF) or the receptor.

DESCRIPTION OF THE DRAWINGS

Not Applicable

DETAILED DESCRIPTION OF THE INVENTION

The present invention provides compositions and methods for capturing platelets at a predetermined site, activating the platelets, and harnessing the natural function of platelets to achieve a beneficial therapeutic result. In accordance with the present invention, platelets may be targeted to a specific site, then the natural ability of platelets to induce thrombus formation may be used to interrupt, disrupt, or reduce blood flow at the site. Reduced blood flow concomitantly reduces nutrient supply to a disease or condition agent, such as a tumor, so the size of the disease agent is diminished. It is clear that reducing the size of a tumor is an obvious therapeutic benefit.

The present invention also provides compositions and methods for indirectly treating a disease or condition by disrupting blood flow to a site or locus of the disease. In this embodiment of the invention. Blood flow is disrupted by positioning platelets at a predetermined site near but not on the site of the disease; activating the platelets; and allowing the natural function of the platelets, e.g., thrombus formation, to reduce and/or eliminate the nutrient supply to the disease site.

The present invention also includes targeting platelets to a predetermined tissue capable of being selectively targeted, e.g., hyperplastic tissue, and activating the platelets. Activating the platelets at the pre-selected site causes a therapeutic benefit by reducing the nutrient supply to the tissue or site.

The present invention provides compositions and methods for inducing thrombus formation by capturing platelets at a selected site, inducing activation of the platelets, and allowing a thrombus to form. By capturing platelets on tumor endothelial cells (an example of a selected site), the compositions and methods of the present invention may be used to treat cancer. Furthermore, the compositions and methods of the present invention provide a therapeutic benefit to the recipient of the composition.

The present invention also provides compositions and methods for treating cancer by inducing platelets to collect at a predetermined site, and activating the platelets, thereby forming a therapeutically beneficial thrombus.

The present invention also provides compositions that include a binding agent having a first binding component and a second binding component, said first binding component targeting the binding agent to the predetermined site, e.g., comprising a binding region for binding the binding agent to the predetermined site; said second binding component comprising a binding region for binding platelets. Such compositions include bifunctional binding agents having an antigenic determinant and a platelet binding site.

Compositions according to the present invention may also include a ligand as a targeting agent, and an anti-ligand for binding the ligand and binding platelets.

Compositions according to the invention may also include one or more of the following: one or more platelet binding modulators (e.g., inhibitors or enhancers), one or more thrombus formation controllers or modulators, or one or more complement cascade components.

Methods according to the invention may also include one or more of the following: administering a binding agent capable of capturing platelets at a pre-determined site; inducing activation of the captured platelets; administering a bifunctional binding agent having an antigenic determinant and a platelet binding site; controlling thrombus generation by altering the temperature of one or more compositions of the invention; and/or altering the temperature at the pre-selected site.

Methods according to the invention may further include one or more of the following administering one or more platelet binding modulators, administering one or more thrombus formation modulators, or administering one or more complement cascade components.

The present invention also includes a kit including a binding agent for targeting a predetermined site and at least one of the following: a binding agent for binding platelets; a ligand for binding the binding agent; a ligand conjugate; an anti-ligand for binding the ligand or the ligand conjugate; a platelet binding modulator (enhancer and/or inhibitor); a thrombus formation modulator; a complement cascade component; a complement cascade component inducer; and a binding agent for binding platelets that includes an anti-ligand. The kit may include a bifunctional binding agent, and/or a binding agent-ligand conjugate, and/or a platelet-binding agent-anti-ligand conjugate.

The compositions and methods of the present invention include any mechanism of delivering a composition to the pre-selected site, including but not limited to systemically, locally, orally, or topically.

In accordance with some embodiments of the invention, binding agents are used to capture platelets at a predetermined site.

Definitions:

As used herein, a binding agent or targeting moiety refers to any chemical or biological molecule for binding one substance to another. Typically the binding agent binds a defined population of cells, typically hyperplastic tissue, or a cancer cell. A molecule's function as a binding agent should not be limited by the structural mechanism of attachment. For example, a binding agent may bind a receptor, an antigenic determinant or epitope, an enzymatic substrate, or other biological structure linking the binding agent to a target cell or cell population. The binding agent may be a conjugate, and includes but is not limited to immunological conjugates, chemical conjugates (covalent or non-covalent), fusion proteins, and the like.

As used herein, a ligand-binding agent refers to a complementary set of molecules that demonstrate specific binding for each other. Preferably, a ligand binding agent is a targeting and a platelet binding agent. A ligand/anti-ligand pair generally binds with relatively high affinity, and for this reason, may be highly desirable for use with the present invention. A very well known ligand/anti-ligand pair is biotin and avidin. As used herein, avidin refers to avidin, streptavidin, neutravidin, derivatives and analogs thereof, and functional equivalents thereof. Avidin may bind biotin or biotin mimetics in a multivalent or univalent manner. Other exemplary ligand/anti-ligand pairs include, but are not limited to, bomophyllic peptides, "leucine zippers", zinc finger proteins/ds DNA fragment, enzyme/inhibitor, hapten/antibody, ligand/receptor, growth factor/growth factor receptor.

As used herein, a selected site, a predetermined sited, targeting, and pre-targeting all refer to the location where the accumulation of platelets will provide a therapeutically beneficial result. Typically this involves target site localization of a targeting moiety. Such sites include but are not limited to the vasculature of solid tumors, tumor associated antigens, tumor specific antigens, hyperplastic tissues, and/or the extracellular matrix or subendothelium that is adjacent to or comprises any of these tissues or cells. The binding agent may be directed against any antigen of clinical significance, but preferably is directed against a tumor-specific or tumor-associated antigen.

As used herein, thrombus refers to any semi-solid aggregate of blood cells enmeshed in fibrin and clumps of platelets. In accordance with the invention, a thrombus is formed as a direct result of activated platelet accumulation at the pre-determined site. Thrombosis refers to the formation of a thrombus, typically within a bloodvessel. Thrombogenic refers to substances that tend to cause thrombosis, or thrombus-forming.

As used herein, therapeutically beneficial, providing a therapeutic benefit or the like refers to a desirable change in the physiology of the recipient animal. In a preferred embodiment of the invention, the change is detectable. In accordance with the invention, any biological mechanism that involves activated platelets or platelet modulation may be used or harnessed to achieve a beneficial therapeutic result. Exemplary therapeutic benefits produced in accordance with the present invention include but are not limited to forming a thrombus, forming a platelet-mediated occlusion, eliminating a hyperplastic tissue or cells, eliminating a tumor and/or tumor cells, diminishing the size of a hyperplastic tissue, diminishing the size of a tumor, causing the hyperplastic tissue or tumor to become susceptible to additional therapies such as chemotherapy and/or radiation therapy or the like, and starving or reducing the nutrient supply to a hyperplastic tissue or cancer.

As used herein, "administering" refers to any action that results in exposing or contacting a composition containing a binding agent with a predetermined cell, cells, or tissue, typically mammalian. Administering may be conducted in vivo, in vitro, or ex vivo. For example, a composition may be administered by injection or through an endoscope or catheter. Administering also includes the direct application to cells of a composition according to the present invention. For example, during the course of surgery, tumor or hyperplastic cells may be exposed. In accordance with an embodiment of the invention, these exposed cells (or tumors) may be exposed directly to a composition of the present invention, e.g., by washing or irrigating the surgical site, and/or the cells.

As used herein, VEGF refers to all members of the Vascular Endothelial Growth Factor family. As used herein, VEGF receptor refers to all members of the Vascular Endothelial Growth Factor Receptor family, including but not limited to FLT1/VEGFR, FLK1/KDR/VEGFR2, and FLT4/VEGFR3. As used herein "causing a tissue or tumor to become susceptible to additional therapies" refers to inducing a condition of low nutrient and/or oxygen supply to the tissue or tumor, through the method of the present invention including, but not limited to, forming a thrombus in the tumor vasculature and/or causing a reduced blood supply to the tumor.

As noted above, the invention employs a binding agent. In accordance with the present invention, the binding agent may function as a targeting agent, a platelet-binding agent, a platelet-activating agent, and/or as a portion of a conjugate for targeting, platelet binding, or platelet activation. In a preferred embodiment of the invention, the binding agent is bifunctional, preferably functioning as a targeting agent and as a platelet-binding agent.

The preferred binding and/or targeting agent is an antibody or antibody-like molecule, preferably a monoclonal antibody. A preferred binding agent is an antibody that binds hyperplastic tissue or cells, including but not limited to a tumor, a tumor associated antigen (TAA), or a tumor specific antigen (TSA). In a preferred embodiment of the invention, the binding agent (i.e., antibody or antibody-like molecules) would bind to the VEGF/VEGF receptor complex. In a further preferred embodiment of the invention, the antibody or antibody-like molecule binding would recognize a neoepitope (cryptic or previously unavailable epitope) formed by the interaction of a ligand and its receptor (e.g., growth factor/growth factor receptor interaction). In a further preferred embodiment of the invention, the binding of the antibody or antibody-like molecules to the ligand/receptor complex (e.g., growth factor/growth factor receptor complex) would not affect the function of either the ligand (e.g., growth factor) or the receptor (e.g., growth factor receptor).

Exemplary binding agents include, but are not limited to: monoclonal antibodies; polyclonal antibodies; native or naked antibodies; chimeric monoclonal antibodies; humanized antibodies; genetically engineered monoclonal antibodies; fragments of antibodies, selected from the group consisting of $F(ab)_2$, $F(ab')_2$, Fab, F(ab'), Dab, Fv, sFv, Fc, and minimal recognition unit; single chains representing the reactive portion of monoclonal antibodies ("SC-Mab"); modified antibodies, e.g. activated or chemically-activated antibodies; tumor-binding peptides; a protein, including receptor proteins; peptide; polypeptide; glycoprotein; lipoprotein, or the like, e.g., growth factors, lymphokines and cytokines; enzymes, immune modulators; hormones, for example, somatostatin; a ligand (with its complementary anti-ligand pair); oligonucleotides; any of the above joined to a molecule that mediates an effector function; and mimics or fragments of any of the above. Analogs of the above-listed targeting moieties that retain the capacity to bind to a defined target cell population may also be used within the claimed invention. In addition synthetic targeting moieties may be designed.

Exemplary binding agents are those that bind to at least one epitope on an antigen or the like disclosed in Nustad, et al, *Tumor Biology*, 17:196–219 (1996) and Nap, et al, *Tumor Biology*, 17:325–331 (1996); *Tumor Biology*, 19:390–420 (1998); and *Tumor Biology*, 19:21–29 (1998).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins, which employ sequences from more than one species. These include but are not limited to the hybridoma technique originally described by Kohler and Milstein [*Nature*, 256:495–497 (1975)]; the human B-cell hybridoma technique [Kozbor, et al., Immunology Today, 4:72 (1983)]; and the EBV transformation technique [Cole, et al., Monoclonal Antibodies and Cancer Therapy, Alan R. Liss, Inc., pp. 77–96 (1985)].

Exemplary proteins useful in the practice of this invention include but are not limited to proteins corresponding to known cell surface receptors (including low density lipoproteins, transferrin and insulin), fibrinolytic enzymes, anti-HER2, platelet binding proteins such as annexins, and biological response modifiers including interleukin, interferon, erythropoietin and colony-stimulating factor). Oligonucleotides, e.g., anti-sense oligonucleotides that are complementary to portions of target cell nucleic acids (DNA or RNA), are also useful as targeting moieties in the practice of the present invention. Oligonucleotides binding to cell surfaces are also useful.

Any growth factor may be used for such a targeting purpose so long as it binds to a tumor or tumor-associated endothelial cell. Suitable growth factors for targeting include but are not limited to VEGF/VPF (vascular endothelial growth factor/vascular permeability factor), FGF (which, as used herein refers to the fibroblast growth factor family of proteins), TGFb (transforming growth factor b), EGF and pleitotropin. Preferably the growth factor receptor to which the targeting factor binds should be present at a higher concentration on the surface of rumor-associated endothelial cells than on non-tumor associated endothelial cells. Most preferably, the growth factor receptor to which the targeting growth factor binds should further be present at a higher concentration on the surface of tumor-associated endothelial cell than on any non-tumor-associated cell type.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

The Fv fragments of immunoglobulins have many significant advantages over whole immunoglobulins for the purpose of targeted tumor therapy, including better lesion penetration on solid tumor tissue and more rapid blood clearance, as well as potentially lower Fc-mediated immunogenicity. An exemplary single-chain Fv (scFv) binding agent may be engineered from the genes isolated from the variable regions of a tumor antibody. For example, a scFv binding agent may comprise a genetically engineered recombinant fusion protein that comprises a heavy chain (Vh) and a light chain (V1) variable domain connected by an artificial linker and an effector domain.

An embodiment of the invention involves a targeting agent having a binding affinity for a marker found, expressed, accessible to binding, or otherwise localized on the cell surfaces of tumor-associated vascular endothelial cells as compared to normal non-tumor-associated vasculature. Further, certain markers for which a targeting agent has a binding affinity may be associated with the tumor-associated vasculature rather than on the tumor-associated endothelial cells, themselves. For example, such markers may be located on basement membranes or tumor-associated connective tissue.

In preferred embodiments of the invention, it will be desirable to prepare and employ an antibody having a relatively high degree of tumor vasculature selectivity, which might be expressed as having little or no reactivity with the cell surface of normal endothelial cells as assessed by immunostaining of tissue section's. Bi-specific antibodies useful in the practice of this aspect of the invention, therefore, will have a dual specificity recognizing a selected tumor cell surface antigen on the one hand, and on the other hand, recognizing a selected platelet specific agent.

Any composition that includes a binding and/or targeting agent according to the invention may be used to initiate in vivo therapeutic benefit, thrombus formation, and/or cell killing or diminution. The composition may include one or more adjuvants, one or more carriers, one or more excipients, one or more stabilizers, one or more permeating agents (e.g., agents that modulated movement across a cell membrane), one or more imaging reagents, one or more effectors; and/or physiologically acceptable saline. Generally, adjuvants are substances mixed with an immunogen in order to elicit a more marked immune response. The composition may also include pharmaceutically acceptable carriers. Pharmaceutically acceptable carriers include but are not limited to saline, sterile water, phosphate buffered saline, and the like. Other buffering agents, dispersing agents, and inert non-toxic substances suitable for delivery to a patient may be included in the compositions of the present invention. The compositions may be solutions suitable for administration, and are typically sterile and free of undesirable particulate matter. The compositions may be sterilized by conventional sterilization techniques.

In a preferred embodiment of the invention, a suitable composition includes a binding agent that binds to an antigen. Typically, the tumor antigen recognized by the bi-specific antibodies employed in the practice of the present invention will be one that is located on the cell surfaces of the tumor being targeted. A large number of solid tumor-associated antigens have now been described in the scientific literature and the preparation and use of antibodies that bind these antigens are well within the skill of the art; of course, the tumor antigen that is ultimately selected will depend on the particular tumor to be targeted.

Exemplary antigens useful as targets in accordance with the present invention include, but are not limited to antigens associated with cancer including but is not limited to lung, colon, rectum, breast, ovary, prostate gland, head, neck, bone, immune system, or any other anatomical location. Exemplary antigens and/or pre-determined sites include but are not limited to GM2, Tn, sTn, Thompson-Friedenreich antigen, Glogo H, Le(y), MUC1, MUC2, MUC3, MUC4, MUC5AC, MUC5B, MUC7, DEA, hCGbeta, HER2/neu, HER2, PSA, PSMA, KSA, CA 72-4, CA 19-9, CA 15-3, CA 125, TAG-72. The subject may be a human or animal subject. Other illustrative tumors and tumor mdarkers are listed in U.S. Pat. Nos. 5,075,218 and 5,776,427.

As noted above, a composition or method of the present invention includes a platelet specific agent or component. Exemplary platelet specific agents or components include but are not limited to von Willebrand factor (VWF), osteopontin, fibrinogen, fibrin, fibronectin, vitronectin, collagen, thrombospondin, laminin, heparin, heparan sulfate, chondroitin sulfate, phospholipase A2, matrix metalloproteinases (MMPs), thrombin, glass, sialyl-lewis X, fibulin-1, platelet-endothelial cell adhesion molecule (PECAM), intercellular adhesion molecule 1 ([CAM-1), ICAM-2, MAC-1, LFA-1, PSGL-1, either singly or in combination.

As noted above, a composition or method of the ptesent invention may include a platelet-mediated occlusion enhancer. The platelet-mediated occlusion enhancer may be a moiety that forms a portion of a bi-functional molecule as noted above, may be an ingredient in a composition according to the invention, and/or may be administered separately from a composition according to the invention. Those skilled in the art will recognize that it may be desirable to include or use a platelet-mediated occlusion enhancer when the individual receiving the therapy is in a state of compromised haemostasis. Under such conditions, the individual receiving the therapy has a propensity to bleed due to a pathological process that may have been acquired or is congenital in nature. Since the utility of the present invention is reliant upon the formation of a thrombus in the tissue or tumor vasculature after targeting platelets to the area, use of methods that augment platelet activation and/or the coagulation process could compensate for the individuals hemorrhagic tendencies. Examples of such conditions include, but are not limited to, haemophilia, von Willebrand's disease, coagulation factor deficiencies, Glanzmann's thrombasthenia, and Bernard Soulier Syndrome.

Exemplary platelet-mediated occlusion enhancers include but are not limited to ristocetin, thrombin, heparin-induced thrombocytopenia (HIT) antibodies or portions thereof, antiphospholipid antibodies (APA) or portions thereof, whole antibody molecules via an Fc-mediated mechanism, anti-LIBS antibodies, anti-CD9 antibodies, epinephrine, thrombin receptor activating peptide (TRAP), cathepsin G, elastase, arachidonate, platelet activating factor (PAF), thromboxane A2 (TxA2), TxA2 mimetics, phospholipase A2 (PLA2), activators of protein kinase C (PKC), adenosine diphosphate (ADP), inducers of cyclo-oxygenase 1 (COX-1), inducers of cyclo-oxygenase 2 (COX-2), collagen, VWF, matrix metalloproteinases (MMPs), heparin, heparan sulfate, chondroitin sulfate, ionophores, complement cascade components (e.g., C5b-9) platelet microparticles, platelet membrane fractions.

As noted above, a composition or method of the present invention may include a platelet-mediated occlusion retarder or the like. The platelet-mediated occlusion retarder may be a moiety that forms a portion of a bi-functional molecule as noted above, may be an ingredient in a composition according to the invention, and/or may be administered separately from a composition according to the invention. Those skilled in the art will recognize that it may be desirable to include or use a platelet-mediated occlusion retarder when the individual receiving therapy based on the method of the present invention has an underlying propensity to thrombose (i.e. form clots too rapidly and/or in inappropriate locations in the body). Although the method of the present invention is directed to the formation of a thrombus in the tumor vasculature, individuals with a propensity to thrombose may form thrombi in inappropriate locations during the course of the therapy described by the present invention. Use of agents to reduce the rapidity and/or extent of thrombosis could be used to minimize the risk of forming thrombi in inappropriate locations in the body. Examples of conditions whereby the individual receiving therapy encompassed by the present invention may require the use of occlusion retarders are, but are not limited to, coronary artery disease, acute myocardial infarction, transient ischemic attack, stroke, high blood pressure, ATIII deficiency, Protein C deficiency, Protein S deficiency, heparin-induced thrombocytopenia, deep vein thrombosis, peripheral vascular disease and/or Factor V Leiden deficiency.

Exemplary platelet-mediated occlusion retarders include but are not limited to aspirin, aspirin-like compounds, non-steroidal anti-inflammatory drugs (NSAIDS), nitric oxide releasing NSAIDS (NO-NSAIDS), ibuprofen, acetaminophen, ketoprofen, ticlopidine, clopidogrel, indomethacin, dipyridamole, omega-3 fatty acids, prostacyclin, nitric oxide, inducers of nitric oxide, inducers of nitric oxide synthase, proanthocyanidins, matrix metalloproteinase inhibitors (MMPIs, TIMs), anti-GPIIb/IIIa agents, anti-$\alpha v \beta 3$ agents, anti-$\alpha 2 \beta 1$ agents, anti-CD36 agents, aurintricarboxylic acid, thrombin receptor antagonists, thromboxane receptor antagonists, streptokinase, urokinase, tissue plasminogen activator (tPA).

In addition, it is known that platelets which have been cooled below their membrane phase transition temperature (i.e., <15 degrees C.) become irreversibly activated. Although the platelets function normally if transfused into a patient, the platelets are rapidly cleared from the body (i.e., approximately 24 hours, in contrast to normal circulating platelet life span of 7 to 10 days). Although these platelets are cleared rapidly, they bind with high avidity to immobilized VWF. Therefore, transfusion of cooled platelets provides an additional means to enhance thrombus formation at the target site. Therefore, one embodiment of the invention includes controlling platelet-mediated occlusion by administering platelets cooled as noted above.

As noted above, the targeting moiety may be, or may be bound to, one member of a binding pair. Methods according to the invention may require a time period sufficient for accumulation of the targeting moiety at the site of localization, for optimal target to non-target accumulation, for accumulation and binding of the second member of the binding pair, and/or for clearance of unbound substances.

In accordance with the invention, three or more step targeting or localization steps may be used. Many of these protocols are well known in the art (see, for example, U.S. Pat. No. 5,578,287 using a biotin/avidin protocol). Exemplary multiple step protocols include, but are not limited to, administering a binding agent-ligand, administering an anti-ligand to clear unbound binding agent and to localize bound binding agent-ligand, and administering an active agent-ligand. As used herein, active agent refers to any therapeutic agent that is active or becomes active and leads to a therapeutic benefit.

In accordance with a method of the invention, the binding agent must be capable of binding a pre-determined binding site or receptor, and may be administered to the patient by any immunologically suitable route. For example, the binding agent may be introduced into the patient by an intravenous, subcutaneous, intraperitoneal, intrathecal, intravesical, intradermal, intramuscular, or intralymphatic route. The composition may be in solution, tablet, aerosol, or multi-phase formulation forms. Liposomes, long-circulating liposomes, immunoliposomes, biodegradable microspheres, micelles, or the like may also be used as a carrier, vehicle, or delivery system. Further more, using ex vivo procedures well known in the art, blood, plasma, serum, or cell components from the patient may be removed from the patient; optionally, it may be desirable to purify the antigen in the patient's blood; the blood, plasma, serum or cellular component may then be mixed with a composition that includes a binding agent according to the invention; and the treated blood, plasma, serum or cellular component is returned to the patient. The clinician may compare the responses associated with these different routes in determining the most effective route of administration. The invention should not be limited to any particular method of introducing the binding agent into the patient.

Administration may be once, more than once, and over a prolonged period. As the compositions of this invention may be used for patients in a serious disease state, i.e., life-threatening or potentially life-threatening, excesses of the binding agent may be administered if desirable. Actual methods and protocols for administering pharmaceutical compositions, including dilution techniques for injections of the present compositions, are well known or will be apparent to one skilled in the art. Some of these methods and protocols are described in Remington's Pharmaceutical Science, Mack Publishing Co. (1982).

A binding agent may be administered in combination with other binding agents, or may be administered in combination with other treatment protocols or agents, e.g., chemotherapeutic agents.

As is well known in the art, a disadvantage associated with administering binding agents or binding agent conjugates in vivo includes non-target or undesirable target binding. It is therefore a desirable attribute of any administered composition to minimize non-target binding, to minimize non-target exposure to the binding agent or active agent, and/or to maximize clearance of non-bound binding agent, ligand, or active agent. Moreover, optimizing these attributes typically permits administering a higher dose of active agent, a therapeutic agent, or an element of the process that activates a previously un-activated agent. Those skilled in the art are well versed in selecting the optimal parameters for administering the highest possible dose while remaining safely below the toxicity threshold.

In accordance with a preferred embodiment of the invention, therefore, un-activated platelets accumulate or are induced to accumulate at a pre-determined site, then the properly localized platelets are selectively activated.

The effectiveness of the present invention may be monitored by conventional assays that determine thrombus formation, morphametric studies of thrombus formation, tumor necrosis, tumor size, tumor morphology, and/or thrombus formation that results in tumor necrosis. One skilled in the art will recognize that other tests may be performed to assess or monitor therapeutic benefit.

Since some binding agents such as proteins are by themselves poor immunogens, their immunogenicity may be augmented by administration in immunological adjuvants and antigen delivery systems. The immunogenicity of a specific composition may also be increased or optimized by choice of delivery route. For example, the immunogenicity of compositions produced in accordance with the present invention that include a monoclonal antibody may be increased by choosing a mode of delivery that increases the direct contact between the binding agent and the antigen. The referred route is intravenous. Those skilled in the art are conversant with the various choices available, and why one route might be chosen over another route for a particular binding agent.

One skilled in the art will also recognize that liposomes, nanospheres, micelles, or microspheres may be used to administer a composition, and that such administration may result in a therapeutically desirable benefit.

It will be recognized by those skilled in the art that for certain congenital and pathological conditions, some of which are listed below, it is desirable to modify a composition or method of the present invention to compensate for a predisposition of the patient to bleed excessively or to thrombose. Under these circumstances, use of modifying agents, which either enhance or dampen a method or composition of the invention, can be employed. The use of these modifying agents is predicted to minimize bleeding or clotting episodes. Moreover, the use of modifying agents enables controlled administration of a composition according to the invention under normal circumstances (i.e., normal hemostasis).

Exemplary conditions that may warrant using controllers, retarders, or agents that diminish a method or composition of the invention include but are not limited to pro-thrombotic or pro-coagulant conditions, such as Factor $V^{leiden}$ deficiency, antiphospholipid syndrome (APS), Protein C and/or Protein S and/or Antithrombin III deficiency, deep vein thrombosis (DVT), pseudo-von Willebrands disease, Type IIb von Willebrands disease, peripheral vascular disease (PVD), and high blood pressure, among others. Exemplary conditions that may warrant using enhancers or agents that augment a method or composition of the invention include but are not limited to any condition that includes a risk of hemorrhage, including but not limited to coagulation factor deficiencies, hemophilia, thrombocytopenia, and anticoagulation therapy, among others. Also, controlling thrombus generation includes at least one of altering the temperature at the predetermined site, altering the rate of blood flow at the pre-determined site, and altering the blood pressure at the predetermined site.

For example, upon initiation of the vascular occlusion process, reversal or dampening of the associated prothrombotic condition may be necessary, as will be recognized by those skilled in the art. In such cases, administration of agents that reduce platelet reactivity will, in turn, reduce response to the vascular occlusion initiators. Such agents are readily known by those skilled in the art and include, but are not limited to: aspirin or aspirin-like compounds, NSAIDS, NO-NSAIDS, ibuprofen, acetaminophen, ketoprofen, ticlopidine, clopidogrel, indomethacin, omega-3 fatty acids, prostacyclin, nitric oxide, inducers of nitric oxide, inducers of nitric oxide synthase, proanthocyanidins, matrix metalloproteinase inhibitors (MMPIs, TIMPs), anti-GPIb agents, anti-GPIIb/IIIa agents, anti-$\alpha v \beta 3$ agents, anti-$\alpha 2 \beta 1$ agents, anti-CD36 agents, aurintricarboxylic acid, thrombin receptor antagonists, thromboxane receptor antagonists, streptokinase, urokinase, tissue plasminogen activator (tPA).

An exemplary process in which it may be desirable to enhance or augment platelet occlusion process includes thrombocytopenic how platelet count) patients. These individuals would benefit from concomitant or pre-administration (transfusion) of platelet products to provide an adequate resource of platelets to accomplish platelet occlusion. It will be recognized by those skilled in the art that all transfusable products mimicking or approximating normal platelet function can be used under such circumstances. Such agents include but are not limited to: random donor platelets, apheresis platelets, autologous platelets, washed platelets, platelet membrane fractions, cooled platelets, frozen platelets, particles containing or expressing platelet membrane components and whole blood.

As a further example, specific platelet-function enhancing agents can be employed to boost or enhance initial platelet reactivity once targeted to the site of therapy. Agents known to those skilled in the art have been demonstrated to enhance existing platelet reactivity and/or lower the threshold limiting sufficient platelet reactivity to facilitate irreversible platelet adhesion and/or platelet degranulation and/or platelet/platelet binding and/or platelet accretion about an existing thrombus. These agents include but are not limited to: ristocetin, thrombin, heparin-induced thrombocytopenia (HIT) antibodies or portions thereof, antiphospholipid antibodies (APA) or portions thereof, whole antibody molecules via an Fc-mediated mechanism, anti-ligand-induced binding site (anti-LUBS) antibodies or portions thereof, anti-CD9 antibodies or portions thereof, epinephrine, thrombin receptor activating peptide (TRAP), cathepsin G, elastase, arachidonate, thromboxane A2 (TxA2) mimetics, TxA2, phospholipase A2 (PLA2), activators of protein kinase C (PKC), adenosine diphosphate (ADP), collagen, VWF, matrix metalloproteinases (MMPs), heparin, heparan sulfate, chondroitin sulfate, ionophores, platelet microparticles, platelet membrane fractions.

An exemplary method of targeting or pre-targeting a composition according to the invention includes accumulating the targeting agent at the target site, then administering a rapidly clearing composition comprising a complementary agent that is capable of binding the previously localized binding agent. Some of these techniques are disclosed in U.S. Pat. No. 4,863,713.

Once introduced into the bloodstream of an animal bearing a tumor, such a bispecific construct will bind to tumor cells within the tumor; bind or immobilize a platelet specific component, whereby immobilization activates the platelet specific component; the activated platelet specific component then binds and activates platelets; and the activated platelets in turn bind and activate other platelets until an occlusion is formed.

EXAMPLES

Example 1

The technique of preparing monoclonal antibodies against antigenic cell surface markers is quite straightforward and may be readily carried out using techniques well known to those of skill in the art as exemplified by the technique of Kohler and Milstein (1975). Generally speaking, the preparation of monoclonal antibodies using stimulated endothelial cells involves the following procedures. Cells or cell lines derived from human tumors are grown in tissue culture for ≧4 days. The tissue culture supernatant ("tumor-conditioned medium") is removed from the tumor cell cultures and added to cultures of human umbilical vein endothelial cells (HUVEC) at a final concentration of 50% (v/v). After 2 days culture the HUVEC are harvested non-enzymatically and 1–2×10$^6$ cells injected intraperitoneally into mice. This process is repeated three times at two-weekly intervals, the final immunization being by the intravenous route. Three days later the spleen cells are harvested and fused with SP2/0 myeloma cells by standard protocols (Kohler and Milstein, 1975): Hybridomas producing antibodies with the appropriate reactivity are cloned by limiting dilution.

From the resultant collection of hybridomas, one will then select one or more hybridomas that produce an antibody that recognizes the activated vascular endothelium to a greater extent than it recognizes non-activated vascular endothelium of course, the ultimate goal is the identification of antibodies having virtually no binding affinity for normal endothelium. Suitable antibody-producing hybridomas are identified by screening using e.g., an ELISA, RIA, IRMA, IEF, or similar immunoassay against one or more types of tumor-activated endothelial cells. Once candidates have been identified, one will desire to test for the absence of reactivity for non-activated or "normal" endothelium or other normal tissue or cell type. In this manner, hybridomas producing antibodies having an undesirably high level of normal cross-reactivity for the particular application envisioned may be excluded.

Example 2

The technique of preparing single chain antibodies that specifically recognize a ligand/receptor complex, specifically a growth factor/growth factor receptor complex is employed, whereby the resulting antibody molecules recognize the growth factor/growth factor receptor complex, but do not bind to either the growth factor or growth factor receptor alone. These antibodies can be formed through the immunization of mice with a complex of purified ligand and receptor, such as VEGF and VEGF receptor, and the resulting V genes used to construct an antibody library in filamentous phage. The phage display of antibody fragments allows the production of recombinant antibody molecules against activated endothelial cell antigens, specifically a ligand/receptor complex. The phage system mimics the vertebrate immune system.

Female Balb/C mice are immunized with HPLC-purified recombinant VEGF and VEGF receptor (e.g. soluble FLT) in complex, in the presence of an adjuvant such as Quil A. After the appropriate antibody titre is reached (approximately the fourth boost), the mice are sacrificed and the spleens isolated. Messenger RNA (mRNA) is isolated from the spleen and transcribed to cDNA. The V genes of the cDNA are amplified and assembled as "single chain Fv" (scFv). After digestion with the appropriate restriction enzymes, the scFv are ligated into phagemid vectors. Competent *E. coli* cells are then transformed with these phagemid libraries, and after infection with helper phage (e.g. M13K07, Pharmacia), phage particles displaying the scFv are prepared. Selected clones are screened for expression of soluble scFv binding to the ligand/receptor complex, but do not bind to either the ligand alone or the receptor alone. This screening is accomplished using standard ELISA techniques, with the ligand/receptor complex, ligand and receptor used as solid-phase antigens, respectively.

Example 3

A variety of endothelial cell markers are known that can be employed as inducible targets for the practice of this aspect of the invention including VEGF/VPF (vascular endothelial growth factor/vascular permeability factor), endothelial-leukocyte adhesion molecule (ELAM-1; Bevilacqua et al., 1987); vascular cell adhesion molecule1 (VCAM-1; Dustin et a]; 1986) intercellular adhesion molecule-1 (CAM-1; Osborn et al., 1989); the agent leukocyte adhesion molecule (LAM-1 agent) or even a major histocompatibility complex (MHC) Class II antigen, such as HLA-DR, HLA-DP, or HLA-DQ (Collins et al., 1984). Of these, the targeting of the VEGF/VEGF receptor complex will be preferred.

Example 4

Targeting platelets to a specific site can take the form of establishing a linkage between the bi-functional binding agent and the target site, followed by platelet binding: or can take the form of establishing a linkage between the bi-functional binding agent and the platelet, followed by binding of the platelet to the target site. The latter example requires pretreatment of the platelets (in vivo, in vitro; autologous donor) with the bifunctional agent. An exemplary bi-functional agent would impart minimal immunogenicity to the treated platelets and would bind specifically with high avidity to the rumor site, tumor vasculature, hyperplastic tissue(s) or organ(s). Platelets pre-treated with the bi-functional agent could take the form of random donor or apheresis platelets suitable for transfusion. Platelets, which have been cooled before or after treatment with the bi-functional agent, would provide a means of enhancing the targeted vaso-occlusive effects.

Example 5

Platelet activation at the target site will induce secondary effects that may enhance diminution or killing of the target tissue. Release of agents by the activated platelets such as platelet factor 4 (PF4) will inhibit angiogenesis. Platelet release of chemoattractants such as Regulated on Activation Normal T-cell Expressed and Secreted (RANTES), post activation, will enhance the effects of leukocytes (e.g., eosinophils, monocytes) on target tissue. Expression of granular constituents such as CD62 by the platelets, post activation, will induce binding of monocytes and polymorphonuclear leukocytes (PMNs) resulting in tissue factor expression (monocyte; procoagulant) and cellular activation and attack (PMNs). In addition, release of CD40 ligand (CD40L) by activated platelet at the target site will induce tissue factor expression by monocytes leading to a local hyper-coagulable state.

Example 6

Identification of Candidate Monoclonal Antibodies

Prostate cancer tumor cell line LnCAP (Clone FGC, ATCC#CRL-1740) was grown in modified RPMI 1640 medium according to the product information sheet provided by the American Type Culture Collection (ATCC). Six different hybridomas producing antibodies specific for MUC1 were tested for binding reactivity to LnCAP cells add MCF-7 cells (human breast carcinoma) by flow cytometry. The following table describes the binding epitope specificity of these hybridomas and the reactivity of the hybridomas with MUC1-expressing MCF-7 human breast carcinoma cells.

| Hybridoma | MUC1 Binding Epitope | Binding to MCF-7 Cells Flow Cytometry (% positive) |
|---|---|---|
| Control | — | 2% |
| TH1 | GVTSAPDTRPAP (Seq. ID No. 1) | 72% |
| TH2 | PDTRP (Seq. ID No. 2) | 69% |
| TH3 | TSAPDTR (Seq. ID No. 3) | 12% |
| TH4 | APDTR (Seq. ID No. 4) | 17% |
| TH5 | TSAPDTR (Seq. ID No. 5) | 11% |
| TH6 | SAPDTRPA (Seq. ID No. 6) | 60% |
| TH1–TH6 Cocktail | — | 55% |

A similar study was carried out using prostate cancer LnCAP cells as the target. Also included in this study was antibody 7E11 (ATCC #FB 10494) recognizing prostate specific membrane antigen (PSMA) and EMT6/Ed (murine mastocytoma) cells as target. The following table presents data from these flow cytometry experiments.

| Antibody | LnCAP | EMT6/Ed |
|---|---|---|
| Control | 8% | 8% |
| 7E11 | 58% | 4% |
| TH1–TH6 Cocktail | 55% | 9% |

Based on these results, the TH6 hybridoma (anti-MUC1) and the 7E11 hybridoma (anti-PSMA) were chosen for further study.

Example 7

Biotinylation of Targeting Antibodies

Protein A Sepharose-purified TH6 and 7E11 monoclonal antibodies were biotinylated according to the manufacturer's (Sigma, St. Louis, Mo.) directions. In addition, humanized (i.e., human Fc bound to mouse monoclonal F(ab')2) antibodies (TH6, 7E 11) were also biotinylated. In a similar manner, purified human von Willebrand factor was also biotinylated. Testing confirmed both significant levels of biotinylation of the antibodies and no reduction in antibody binding to LnCAP cells. Similarly, biotinylated VWF was shown to retain both the capacity to initiate platelet adhesion and promote platelet/platelet binding, post biotinylation. VWF (±biotinylation) was immobilized on polystyrene beads as described by Stewart et al (Br J Haematol, 97:321–329, 1997). The VWF-coated beads were then used as a solid-phase agonist to induce platelet adhesion and subsequent platelet dense granule ATP release. ATP release was quantified using a luciferin/luciferase assay (Stewart et al, 1997). Comparison of VWF beads with biotinylated-VWF beads indicated the two agents to be equivocal relative to platelet activation (0.41±0.05, 0.39±0.05 arbitrary luminescence units; respectively).

Example 8

Targeting Platelets to Cancer Cells

LnCAP cells were challenged with biotinylated antibodies, or non-biotinylated antibodies (TH6 or 7E 11); washed to remove unbound antibody; challenged with avidin or neutravidin, or not; washed to remove unbound avidin or neutravidin; challenged with biotinylated human VWF; then incubated with human citrated whole blood or platelet rich plasma under agitation. Platelet reactivity with the LnCAP cells was then assessed by video microscopy, phase contrast microscopy and fluorescence microscopy. The following table presents the results of these experiments.

| Test Conditions | Human Platelets Binding to LnCAP Cells |
|---|---|
| Control - No agents added to LnCAPs | – |
| TH6.biotin/No Avidin/VWF.biotin | – |
| TH6.biotin/Avidin/VWF.biotin | ++ |
| Humanized TH6.biotin/No Avidin/VWF.biotin | –/+ |
| Humanized TH6.biotin/Avidin/VWF.biotin | ++++ |
| 7E11.biotin/No Avidin/VWF.biotin | – |
| 7E11.biotin/Avidin/VWF.biotin | +++ |
| Humanized 7E11.biotin/No Avidin/VWF.biotin | –/+ |
| Humanized 7E11.biotin/Avidin/VWF.biotin | ++++ |

Targeting of the LnCAP cells with either biotinylated TH6 or 7E11 led to localization of platelets, in either platelet rich plasma or whole blood, to the cancer cells, via interaction with cancer cell-immobilized VWF. The interaction of platelets with cancer cells was dramatically enhanced by constructing a humanized/biotinylated targeting antibody. Engagement of the platelet Fc receptor by the humanized portion of the targeting antibody (i.e., the human Fc component) caused massive platelet aggregation about the cancer cells and subsequent membrane blebbing and/or loss of cell membranes in the form of vesicles.

Although the present invention has been described in terms of particular preferred embodiments, it is not limited to those embodiments. Alternative embodiments, examples, and modifications, which would still be encompassed by the invention, may be made by those skilled in the art, particularly in light of the foregoing teachings.

We claim:

1. A method of inducing a thrombus in vivo comprising:
administering a first agent that is a binding agent having
   a) a first component comprising an antibody or an antigen binding portion thereof that binds to a preselected site selected from the group consisting of tumor-associated antigens and tumor-specific antigens and
   b) a second component comprising a first ligand;
administering an anti-ligand that specifically binds to the first ligand;
administering a second agent that specifically binds to platelets, the second agent comprising von Willebrand factor and a second ligand that specifically binds to the anti-ligand; and
binding platelets on the second agent and inducing activation of the platelets;
thereby inducing a thrombus in vivo, wherein the first and second ligands and the anti-ligand consist of a complementary set of molecules that specifically bind to each other and are selected from the group consisting of biotin/avidin, zinc finger protein/dsDNA fragment, enzyme/inhibitor, hapten/antibody, ligand/receptor, homophylic peptides and leucine zipper sets.

2. The method of claim 1, wherein the first and second ligands are biotin and the anti-ligand is avidin.

3. The method of claim 1, wherein the avidin is selected from the group consisting of streptavidin and neutravidin.

4. The method of claim 1, wherein the ligand/receptor set is VEGF/VEGF receptor.

5. The method of claim 1, wherein at least one ligand or the anti-ligand comprises a human Fc fragment.

* * * * *